United States Patent [19]
Friedman

[11] Patent Number: 4,501,585
[45] Date of Patent: Feb. 26, 1985

[54] MOTHER'S MILK HARVESTING AND COLLECTION DEVICE

[76] Inventor: Laura L. Friedman, 6348 Trotwood, Portage, Mich. 49008

[21] Appl. No.: 410,381

[22] Filed: Aug. 23, 1982

[51] Int. Cl.³ .............................................. A61F 5/44
[52] U.S. Cl. .................................. 604/346; 604/355; 141/338; 215/11 E
[58] Field of Search ............... 128/760, 762, 765, 767, 128/771, 774, 359, 360; 604/317, 323, 346, 347, 350, 351, 352, 353, 74–76; 119/146; 242/105; 206/390; 141/337, 338; 215/11 R, 11 E, DIG. 3; 383/36, 904

[56] References Cited

U.S. PATENT DOCUMENTS

| | | | |
|---|---|---|---|
| 1,719,982 | 7/1929 | Keith | 604/346 |
| 2,987,209 | 6/1961 | Leonard | 215/11 E |
| 3,204,855 | 9/1965 | Bognton et al. | 215/11 E |
| 3,707,969 | 1/1973 | Sanford | 604/353 |
| 3,797,734 | 3/1974 | Fleury et al. | 383/36 |
| 3,888,236 | 6/1975 | Marx | 604/323 |
| 3,923,040 | 12/1975 | Beach | 141/338 |
| 4,016,975 | 4/1977 | Hammer | 206/390 |
| 4,294,582 | 10/1981 | Naslund | 128/767 |
| 4,335,730 | 6/1982 | Griffin | 604/317 |

Primary Examiner—C. Fred Rosenbaum
Assistant Examiner—J. Kruter
Attorney, Agent, or Firm—Gordon W. Hueschen

[57] ABSTRACT

A mother's-milk harvesting device, suitable for the collection of mother's milk from a human milk-providing breast, in the form of an essentially liquid-tight receptacle comprising an upper breast-receiving portion and a lower milk-receiving portion, the upper portion when in use being adapted for the reception of a breast therein, and the lower portion being in internal communication with the upper portion and being adapted to permit its disposition in a plastic-film-baby-bottle holding device, preferably formed of plastic film and adapted to be flat-folded; such device wherein a line of weakness is present between the upper portion and the lower portion, especially wherein a second line of weakness is located in spaced relationship to the first line of weakness a distance sufficient to define a top section in the bottom portion for facilitating removal of the top section of the bottom portion when the bottom portion is severed from the top portion, placed in a plastic-film-baby-bottle holder, and turned down along the upper rim thereof; and such device in combination with a retention means adapted for temporary but removable retention of the upper portion of the device around a human breast, are disclosed.

13 Claims, 13 Drawing Figures

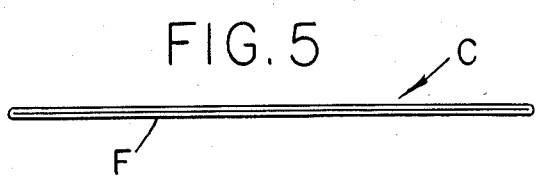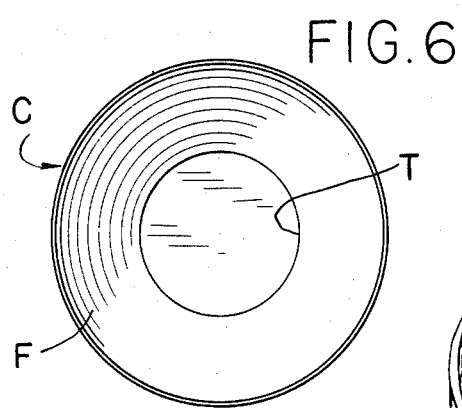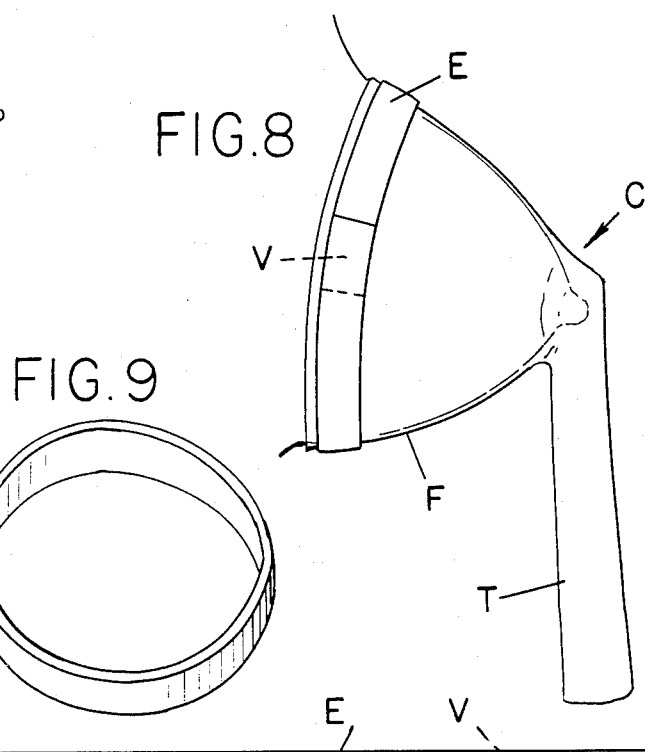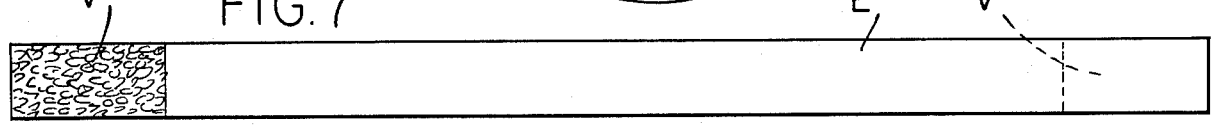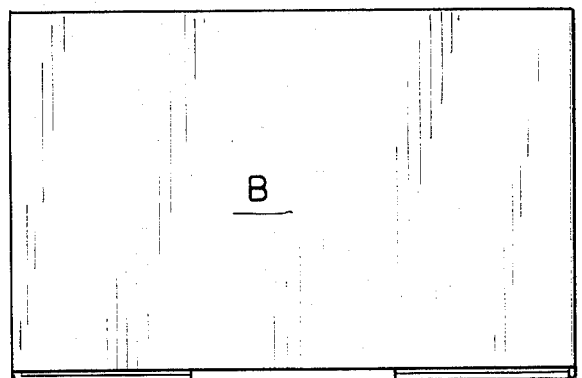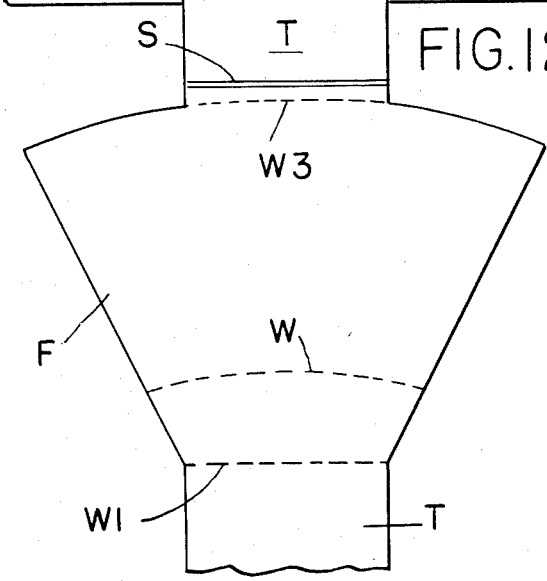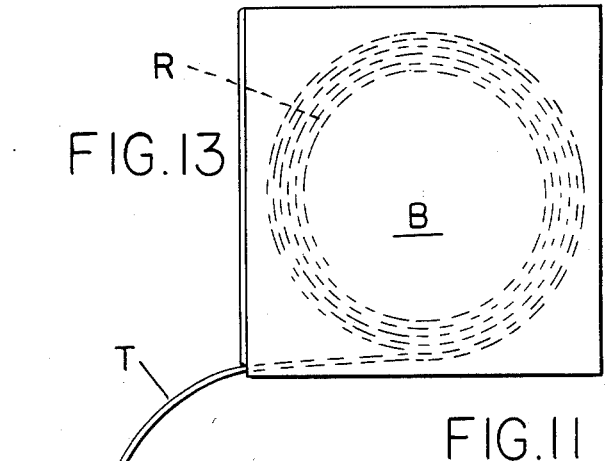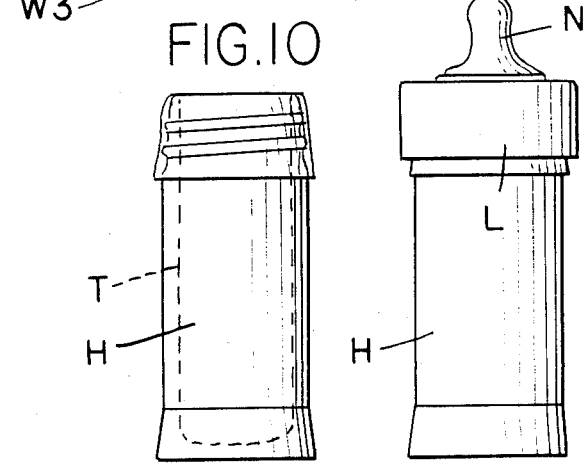

MOTHER'S MILK HARVESTING AND COLLECTION DEVICE

BACKGROUND OF INVENTION

1. Field of Invention

Devices for harvesting or collecting mother's milk.

2. Prior Art

None known. To the best of my knowledge, when it has been desired to harvest mother's milk in the past, this has been done simply by collecting the same in a plastic bag, bottle, or the like, and no particular device especially designed for the harvesting of mother's milk and especially adapted for that purpose, especially with all the advantages of the presently-presented device, has heretofore been known.

It is, however, well known that mother's milk is today highly regarded from the standpoint of nutrition and that breast feeding is highly recommended by most if not all pediatricians. It is also well known that excessive milk production can lead to extreme discomfort and the necessity of breast pumping which is itself extremely uncomfortable. Further, when mother's milk has been collected, it has ordinarily been collected by stripping to relieve the discomfort where breast pumping was not employed. Moreover, it is also well known that, as a mother breast feeds her infant from one breast, the milk "lets down" bilaterally, by which is meant that the available mother's milk exudes from both breasts. It is at this time that the collection of breast milk is most effectively carried out, in view of the fact that the mother's milk can be collected on the side or from the breast not being used for feeding. The amount may vary from one ounce to two ounces, more or less. The device of the invention is not limited to employment during feeding, but of course can be employed at any time when the mother feels that her milk "lets down". Since breast milk can be frozen for up to several weeks in an ordinary refrigerator/freezer and up to six months in a chest or deep freezer, preservation of the mother's milk is now a simple matter. Additional collections can be added to previously frozen collections but, to prevent spoilage, additional collections should be cooled before adding to already frozen mother's milk. Milk may, of course, be stored in a simple plastic bag and then poured into a conventional infant feeding bottle for administration, but this is generally inconvenient and employs a plurality of steps and suffers from the essential drawback of collecting in a plastic bag and pouring therefrom, where the bag is not particularly adapted for the purpose involved.

For the more convenient harvesting and utilization of the extremely valuable mother's milk, it is apparent that an improved harvesting and utilization device would be highly desirable and would fulfill a long-standing need in the art.

OBJECTS OF THE INVENTION

It is accordingly an object of the present invention to provide an improved mother's milk harvesting device which is particularly adapted for the collection of mother's milk and likewise particularly adapted for its storage and utilization in a normal type of plastic-film-baby-bottle holder or dispenser. Plastic-film-baby-bottles are now well established in the art, as are the holders therefor, which are designed to accomodate the plastic-film-baby bottles within a hollow cylinder, have the top of the plastic-film-baby-bottle turned back over the outside of the cylinder, and have means including the usual rubber or elastomeric nipple secured at the top of said column over the down-turned edge of the plastic-film-baby-bottle, which edge may then be removed, conveniently along a line of weakness provided therein. It is another object of the invention to provide an improved mother's milk harvesting device which has an upper portion which is particularly adapted for receiving a breast therein and which has a lower portion which is severable from the upper portion and which is particularly adapted to permit its disposition in a plastic-film-baby-bottle holding device of the type just described. Another object of the invention is to provide such a device which prevents waste of breast milk, which provides means for collection and storage of breast milk for future feeding, which adapts to nursing systems of the type previously described and which are presently available on the open market, which eliminates the necessity of uncomfortable breast pumping, which may be provided in sterile form, and which is readily disposable. Other objects of the invention will appear hereinafter and still other objects will be apparent to one skilled in the art.

The foregoing and additional objects are achieved by provision of the novel mother's milk harvesting device of the present invention.

SUMMARY OF THE INVENTION

My invention may be summarized, inter alia, by the following description:

a mother's-milk harvesting device, suitable for the collection of mother's milk from a human milk-providing breast, in the form of an essentially liquid-tight receptacle comprising an upper breast-receiving portion and a lower milk-receiving portion, said upper portion when in use being adapted for the reception of a breast therein, and said lower portion being in internal communication with said upper portion and being adapted to permit its disposition in a plastic-film-baby-bottle holding device; such device wherein said upper portion is generally frustoconical and said lower portion is generally cylindrical; such device wherein said device is formed of plastic film; such device wherein said device is adapted to be flat-folded; such device wherein a plurality of such flat-folded devices are connected by lines of weakness; such device wherein such plurality of sheetform devices is adapted to be dispensed in a roll; such device wherein a line of weakness is present between said upper portion and said lower portion; such device wherein a second line of weakness is present adjacent but in spaced relation to said first line of weakness; such device wherein said second line of weakness is located in spaced relationship to said first line of weakness a distance sufficient to define a top section in said bottom portion for facilitating removal of said top section of said bottom portion when said bottom portion is severed from said top portion, placed in a plastic-film-baby-bottle-holder, and turned down along the upper rim thereof; such device in combination with a retention means adapted for temporary but removable retention of said upper portion of said device around a human breast; such combination wherein said retention means is in the form of an elastic strap; such combination wherein said strap is provided with means for securing the ends thereof to each other when placed around a human breast; and such combination wherein said retention means is in the form of a circular elastic loop and, finally, such device wherein a line of weakness is also present in the upper breast-receiving portion for tearing off a portion thereof for adaptability of said device to different breast dimensions.

DESCRIPTION OF THE PREFERRED EMBODIMENTS OF THE INVENTION

Figure 1:
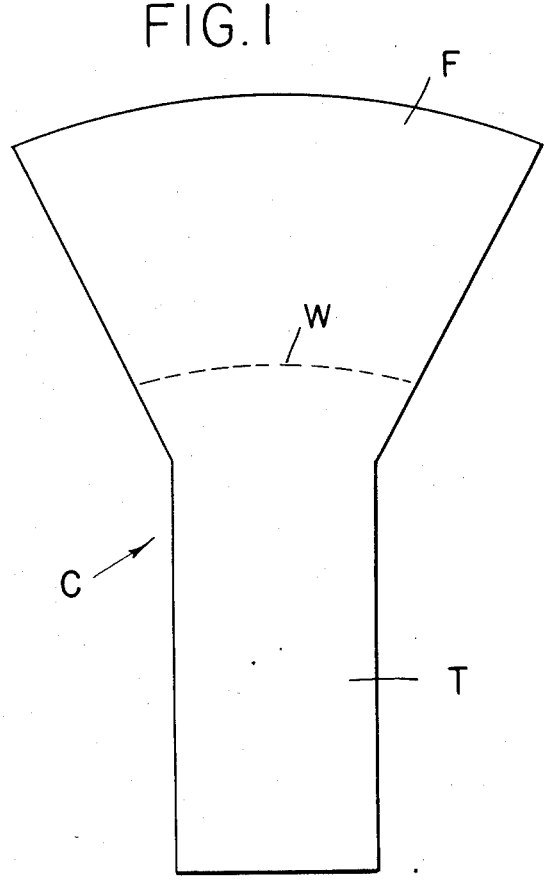
Figure 2:
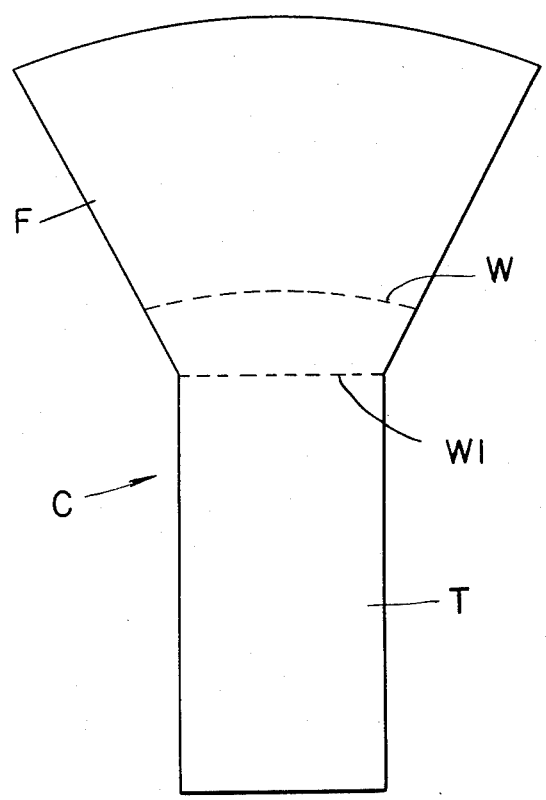
Figure 3:
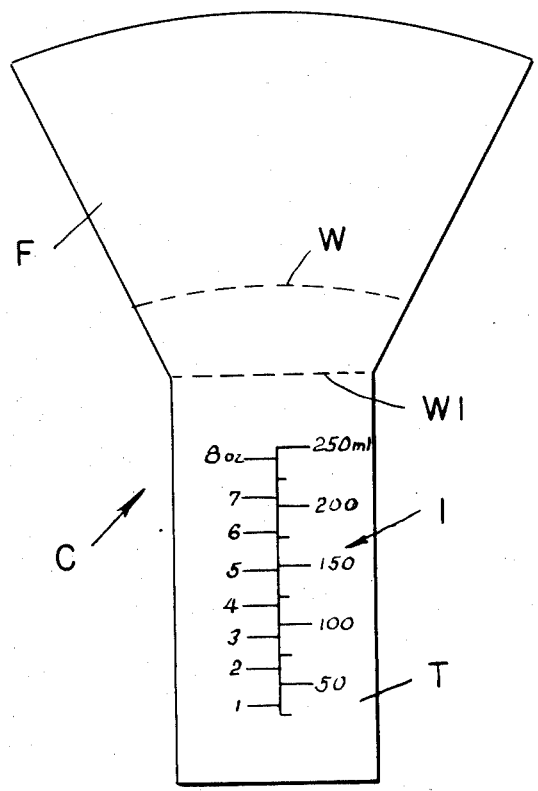
Figure 4:
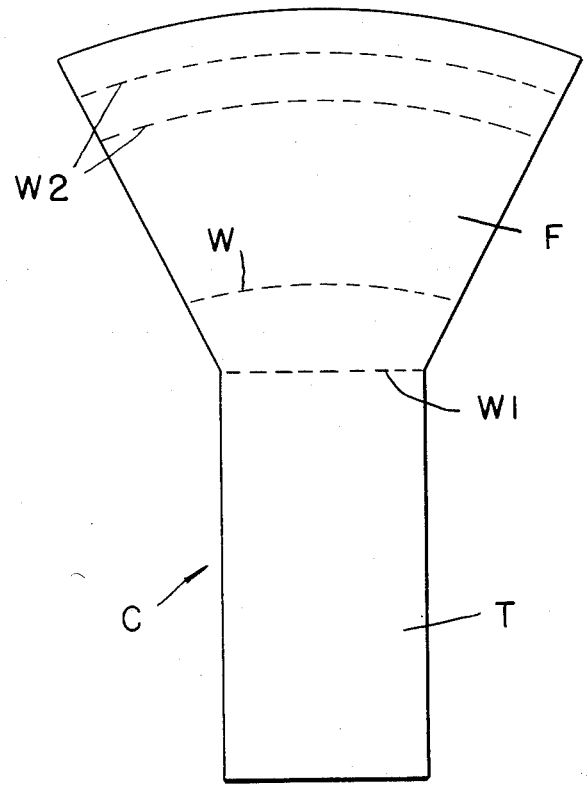

The invention, in several preferred embodiments, is illustrated by the accompanying drawings, in which:

FIG. 1 is a face view of the simplest form of my invention,

FIG. 2 is a modification of my invention with a second line of weakness or "tear-apart" scoreline, FIG. 3 is a modification like that of FIG. 2 with an ounce and milliliter scale added, FIG. 4 is a modification with additional lines of weakness of "tear-apart" scorelines for adaptation to a smaller breast, FIG. 5 is a top view of a device according to my invention, in the flattened form in which marketed, FIG. 6 is a top view of a device according to my invention formed into a circular shape and ready for use, FIG. 7 is a top plan view of an elastic strap having Velcro ® ends, FIG. 8 shows the harvesting or collecting unit of the invention applied to a breast, FIG. 9 shows a garter or circular elastic loop which may be used as a temporary retention means instead of the strap of FIG. 7, FIG. 10 shows the filled lower milk-collecting portion of the harvesting device of my invention set in a standard nursing bottle holder, FIG. 11 is like FIG. 10 but with a cap and nipple in place, FIG. 12 shows a plurality of collector or harvester units according to the invention in strip form dispensing from a carton with one harvesting unit ready to be ripped off along a line of weakness; and FIG. 13 shows a side view of the dispenser of FIG. 12 with one harvester or collector unit removed.

DETAILED DESCRIPTION OF THE INVENTION

The mother's-milk harvesting or collecting device is shown generally at C in FIGS. 1 through 4. It has a closed bottom, as may be effected by sealing, as shown at S in FIG. 12 or otherwise as is well known in the art. The harvester device as shown is in the form of an essentially liquid-tight receptacle comprising an upper breast-receiving portion F, which is of frustroconical or funnel shape and, in internal communication therewith, a lower milk-receiving portion or tube T, which lower portion T is adapted to permit its disposition in a usual nursing bottle holder such as a plastic-film-baby-bottle holding device. A line of weakness is shown at W, this line of weakness being for purposes of severing lower portion T from upper portion F.

In FIG. 2 there is shown a second line of weakness W1, this line of weakness being provided for purposes of severing a top section of the lower portion of the collection or harvesting device C from the remainder of the bottom or lower portion T after placing it in a plastic-film-baby-bottle holder and turning the upper portion of the lower portion T down along the upper rim of the bottle holder. As shown in FIG. 10, this top section of the lower portion C of the collection device has been severed after turning it down around the upper edge of the holder H.

In FIG. 3 is shown a further variation of the mother's milk harvesting device of my invention wherein indicia are provided in the lower portion or tube portion T thereof, as shown this indicia being in terms of both ounces and milliliters, although either of these indicia or other indicia may also be employed if desired.

The modification of FIG. 4 shows two additional lines of weakness W2, for purposes of enabling the upper breast-receiving portion to be adapted to smaller breasts, if desired. In such case, it is only necessary to sever a portion of the upper frustroconical top portion F along either line of weakness W2, to produce a funnel-shaped top portion which is adapted to receive a smaller breast.

The harvesting device of the invention is shown in flat-folded form, as it is marketed, in FIG. 5, and in its expanded or circular form, ready for use, in FIG. 6.

In FIGS. 7 and 8 are shown retention means adapted for temporary but removable retention of the upper portion of the device of the invention around a human breast, the retention means in FIG. 7 being in the form of an elastic strap E having means for securing the ends thereof to each other, when placed around a human breast, at each end thereof. As shown in FIG. 7 these means are Velcro ® piling as shown at V. In FIG. 9 is shown an alternate retention means in the form of a garter or circular elastic loop G. In FIG. 8 is shown the harvesting device C applied to a human breast, and removably retained thereabout by retention means E in the form of the elastic strap of FIG. 7 having securing means at the ends thereof in the form of the Velcro ® piling. The top portion or funnel-like portion F is indicated as surrounding the human breast, whereas the lower portion or milk-receiving portion T is shown hanging vertically therefrom for collection of mother's milk therein.

The device of the invention is particularly well-adapted to be marketed in flat-folded form and particularly wherein a plurality of such flat-folded devices are connected along lines of weakness, such as W3 in FIG. 12. FIG. 12 shows a box or dispensing carton B, with the collecting or harvesting devices arranged in strip form and emanating from the dispensing carton with one unit ready to be torn off along line of weakness W3, located just beyond and in spaced relation to seal line S defining the bottom of lower milk-receiving portion T. The manner of dispensing such plurality of units as shown in FIG. 12 in roll form is illustrated in FIG. 13 wherein roll R is located within box or dispensing container C with one lower portion T protruding therefrom, having been removed from the preceding portion along line of weakness W3.

As already indicated, the lower or milk-receiving portion C of the device of the invention is shown in FIG. 10 supported in a standard nursing bottle holder which is of the nature of a plastic-film-baby-bottle holding device, the lower or milk-receiving portion T being illustrated in dotted lines and having an upper portion thereof turned down all along the upper rim of the holder. A top section of said bottom portion T has been removed by tearing along the line of weakness W1 after severing said bottom portion T from said top portion F along the line of weakness W and placing said bottom or milk-receiving portion T within said plastic-film-baby-bottle holding device H, if desired after freezing or other method of preservation. FIG. 11 shows the same thing as FIG. 10, but with cap or lid L, supporting nipple N, screwed in place atop said holder H and, with mother's milk content within tube or milk-receiving portion T, ready for infant feeding in the normal manner.

In application, the device of the invention may be applied to a bare breast with the upper breast-receiving portion of frustoconical or funnel shape placed over the breast. The upper portion of the device is then pulled up close to the chest, making certain that the underside of the breast is fully covered. The upper portion of the device is then secured in place by the retention means, such as by stretching the elastic band around the breast close to the chest and adjusting the same for a comfortable fit. When the mother is wearing a nursing brassiere, the device of the invention, especially the upper portion thereof, may be tucked into the brassiere, again making certain that the underside of the breast is fully covered. Any milk "letting down" from the unused breast, or from the breast being stripped if such is the case, is channeled from the upper portion to the lower portion of the device, with which it is in internal communication, thereby collecting the same in the lower portion of the device. When the mother is ready to switch sides or breasts for feeding, or discontinue stripping, or when let down has ceased, it is a simple matter to remove the device from the breast, sever the upper portion from the lower portion as along the line of severance, secure the top of the lower portion with a rubber band or other securing means, label and/or date the same, and introduce it into a freezer. When it is desired to administer the frozen mother's milk, it is a simple matter to remove the same from the freezer, thaw the same under water (boiling on a stove is not recommended in view of the high incidence of curdling), introduce the lower portion of the device into a normal cylindrical plastic-film baby bottle holder within the hollow column thereof, turn down the upper edge of the lower portion of the device over the rim of the column, and secure the nipple to the upper end thereof for immediate infant feeding. In cases where the second line of weakness is provided, it is a simple matter to remove the remaining flange of the device from around the outside edge of the holder. In cases where a further line of weakness or several further lines of weakness are provided, as indicated in the drawings, it is a simple matter to sever the frustroconical or breast-receiving portion of the device along such additional line or lines of weakness, thereby to adapt the upper frustroconical or funnel-shaped portion for employment with a breast of smaller dimensions.

The material of construction is not limiting, but is preferably a sheetform material, advantageously of plastic film, such as polyester, polyurethane, or polyethylene, and of a type which can readily be sterilized if desired. The upper portion of the device may be made in one size, which generally adapts to all breast sizes, or the upper frustoconical portion may be provided in different sizes thereby providing different sized cups as is usual in the brassiere art. The imprinting of contents on the lower portion or collecting portion of the device of the invention, according to volume or weight, is of course optional, but extremely convenient from the standpoint of the user.

It is thereby seen that, according to the present invention, a unique and extremely valuable mother's milk harvesting device has been provided, and that all of the objects of the invention have been fulfilled.

It is to be understood that the invention is not to be limited to the exact details of operation or to the exact compounds, compositions, methods, procedures, or embodiments shown and described, as numerous modifications and equivalents will be apparent to one skilled in the art and may be made without departing from the spirit or scope of the invention, which is therefore to be limited only by the full scope of the appended claims.

I claim:

1. A collapsible mother's-milk harvesting device, suitable for the collection of mother's milk from a human milk-providing breast, adapted, in the collapsed mode to lie flat and, in the opened-up mode to form an essentially single integral liquid-tight receptacle comprising an upper breast-receiving portion means and a lower milk-receiving portion, said upper portion means, in the opened-up mode, being adapted for the reception of a breast therein, and said lower portion means, in the same mode, being in internal communication with said upper portion means and having a size and shape to permit its disposition in a plastic-film-baby-bottle holding device as the milk-containing container-liner thereof, and said lower portion means having an upper section adapted to be rolled down over the open end of a plastic-film-baby-bottle holding device having an outer wall and to be held in place thereon between the outer wall thereof and a wall of a nipple.

2. The device of claim 1 wherein, in the opened-up mode, said lower portion means is generally cylindrical and said upper portion means flares out therefrom in a generally frustroconical pattern.

3. The device of claim 1 wherein said device is formed of plastic film and any cross-section of said device in the collapsed mode has no more than two layers of said film.

4. The device of claim 1, in combination with a plastic-film-baby-bottle holding device.

5. A mother's-milk harvesting device, suitable for the collection of mother's milk from a human milk-providing breast, in the form of an essentially liquid-tight receptacle comprising an upper breast-receiving portion means and a lower milk-receiving portion means, said upper portion being adapted for the reception of a breast therein, and said lower portion means being in internal communication with said upper portion means and having a size and shape to permit its disposition in a plastic-film-baby-bottle holding device as the milk-containing container-liner thereof, wherein a line of weakness is present between said upper portion means and said lower portion means to permit separation thereof.

6. The device of claim 5, wherein a second line of weakness is present adjacent but in spaced relation to said first line of weakness.

7. The device of claim 6, wherein said second line of weakness is located in spaced relationship to said first line of weakness a distance sufficient to define a top section in said bottom portion means for facilitating removal of said top section of said bottom portion means when said bottom portion is severed from said top portion means placed in a plastic-film-baby-bottle holder, and turned down along the upper rim thereof.

8. A mother's-milk harvesting device, suitable for the collection of mother's milk from a human milk-providing breast, in the form of a liquid-tight receptacle comprising an upper breast-receiving portion means and a lower milk-receiving portion, said upper portion being adapted for the reception of a breast therein, and said lower portion means being in internal communication with said upper portion means and having a size and shape to permit its disposition in a plastic-film-baby-bottle holding device as the milk-containing container-liner thereof, in combination with a retention means adapted for temporary but removable retention of said upper portion means of said device around a human breast.

9. The combination of claim 8, wherein said retention means is in the form of an elastic strap.

10. The combination of claim 9, wherein said strap is provided with means for securing the ends thereof to each other when placed around a human breast.

11. The combination of claim 8, wherein said retention means is in the form of a circular elastic loop.

12. A mother's-milk harvesting device, suitable for the collection of mother's milk from a human milk-providing breast, in the form of an essentially liquid-tight receptacle comprising an upper breast-receiving portion and a lower milk-receiving portion, said upper portion when in use being adapted for the reception of a breast therein, and said lower portion being in internal communication with said upper portion and being adapted to permit its disposition in a plastic-film-baby-bottle holding device, wherein a line of weakness is present between said upper portion and said lower portion, and wherein a line of weakness is also present in the upper breast-receiving portion for tearing off a portion thereof for adaptability of said device to different breast dimensions.

13. A mother's-milk harvesting device, suitable for the collection of mother's milk from a human milk-providing breast, in the form of a liquid-tight receptacle comprising an upper breast-receiving portion means and a lower milk-receiving portion, said upper portion means being adapted for the reception of a breast therein, and said lower portion means being in internal communication with said upper portion means and having a size and shape to permit its disposition in a plastic-film-baby-bottle holding device as the milk-containing container-liner thereof, wherein a line of weakness is present in the upper breast-receiving portion means for tearing off a portion thereof for adaptability of said device to different breast dimensions.

* * * * *

UNITED STATES PATENT AND TRADEMARK OFFICE
CERTIFICATE OF CORRECTION

PATENT NO. : 4,501,585

DATED : February 26, 1985

INVENTOR(S) : Laura L. Friedman

It is certified that error appears in the above-identified patent and that said Letters Patent is hereby corrected as shown below:

Col. 6, line 16; after "portion" (first occurrence) insert -- means --

Col. 6, line 40; after "essentially" insert -- single integral --

Col. 6, line 43; after "portion" insert -- means --

Col. 6, line 60; after "portion" insert -- means --

Col. 6, line 61; after "means" insert a comma -- , --

Col. 6, line 67; after "portion" (both occurrences) insert -- means -- (both occurrences)

Col. 8, line 12; after "portion" (first occurrence) insert -- means --

Signed and Sealed this

Twenty-fourth Day of September 1985

[SEAL]

Attest:

DONALD J. QUIGG

Attesting Officer

Commissioner of Patents and
Trademarks—Designate